(12) United States Patent
Biemold et al.

(10) Patent No.: US 9,880,400 B2
(45) Date of Patent: Jan. 30, 2018

(54) OPHTHALMIC LENS FOR CORRECTING ASTIGMATISM

(71) Applicant: Ophtec B.V., Groningen (NL)

(72) Inventors: Peter Biemold, Groningen (NL); Erik de Haas, Groningen (NL); Alfred Willem Wassenburg, Groninberg (NL)

(73) Assignee: Ophtec B.V., Groningen (NL)

( * ) Notice: Subject to any disclaimer, the term of this patent is extended or adjusted under 35 U.S.C. 154(b) by 0 days.

(21) Appl. No.: 15/029,531

(22) PCT Filed: Oct. 6, 2014

(86) PCT No.: PCT/NL2014/050691
§ 371 (c)(1),
(2) Date: Apr. 14, 2016

(87) PCT Pub. No.: WO2015/050455
PCT Pub. Date: Apr. 9, 2015

(65) Prior Publication Data
US 2016/0299355 A1 Oct. 13, 2016

(30) Foreign Application Priority Data
Oct. 4, 2013 (EP) .................................... 13187458

(51) Int. Cl.
*G02C 7/00* (2006.01)
*G02C 7/04* (2006.01)
*A61F 2/16* (2006.01)

(52) U.S. Cl.
CPC .............. *G02C 7/047* (2013.01); *A61F 2/164* (2015.04); *A61F 2/1637* (2013.01); *G02C 7/04* (2013.01);
(Continued)

(58) Field of Classification Search
CPC .......... G02C 7/047; G02C 7/045; G02C 7/04; G02C 2202/06; G02C 2202/22; A61F 2/164; A61F 2/1637
(Continued)

(56) References Cited

U.S. PATENT DOCUMENTS

| 3,722,986 A | 3/1973 | Tagnon |
| 5,125,729 A | 6/1992 | Mercure |

(Continued)

FOREIGN PATENT DOCUMENTS

| EP | 0107444 A2 | 5/1984 |
| EP | 0571320 A1 | 11/1993 |

(Continued)

OTHER PUBLICATIONS

Marcos et al., "The depth-of-field of the human eye from objective and subjective measurements", Vision Research, vol. 39, (1999), pp. 2039-2049.

(Continued)

*Primary Examiner* — Tuyen Tra
(74) *Attorney, Agent, or Firm* — Akerman LLP (57) ABSTRACT

An ophthalmic lens to be worn on or in a human eye for refractive correction of astigmatism. The lens has an anterior surface and a posterior surface shaped such that at least a zone of the lens said lens has a first dioptric power over a first main meridian, a second dioptric power different from the first dioptric power over a second main meridian intersecting the first meridian, and a dioptric power between the first dioptric power and said second dioptric power over each meridian between the first and second main meridians, the optical power continuously varying from meridian to meridian. The main meridians and at least one meridian between the main meridians each have a different Coddington shape factor and a different asphericity that is related to (Continued)

the Coddington shape factor of the respective meridian in accordance with a relationship providing aberration neutral refraction for the respective meridian.

8 Claims, 5 Drawing Sheets

(52) U.S. Cl.
CPC ......... *G02C 7/045* (2013.01); *G02C 2202/06* (2013.01); *G02C 2202/22* (2013.01)

(58) Field of Classification Search
USPC ....... 351/159.06, 159.05, 159.02, 159.01, 41
See application file for complete search history.

(56) References Cited

U.S. PATENT DOCUMENTS

| | | | |
|---|---|---|---|
| 5,512,220 | A | 4/1996 | Roffman et al. |
| 5,695,509 | A | 12/1997 | El Hage |
| 5,969,790 | A | 10/1999 | Onufryk |
| 6,457,826 | B1 | 10/2002 | Lett |
| 6,537,545 | B1 | 3/2003 | Karageozian et al. |
| 8,167,940 | B2 | 5/2012 | Hong et al. |
| 2003/0014107 | A1 | 1/2003 | Reynard |
| 2006/0116763 | A1 | 6/2006 | Simpson |
| 2009/0132041 | A1 | 5/2009 | Fiala et al. |
| 2010/0315589 | A1 | 12/2010 | Portney |
| 2012/0147321 | A1 | 6/2012 | Portney |

FOREIGN PATENT DOCUMENTS

| | | |
|---|---|---|
| EP | 0742461 A2 | 11/1996 |
| EP | 0949529 A2 | 10/1999 |
| WO | 97/16760 A1 | 5/1997 |
| WO | 0203126 A1 | 1/2002 |
| WO | 2004/090611 A2 | 10/2004 |

OTHER PUBLICATIONS

Saldanha et al., "Postoperative rotation of a 3-piece loop-haptic acrylic intraocular lens", J Cataract Refract Surg, vol. 35, Oct. 2009, pp. 1751-1755.

Meister, D., "Principles of Atoric Lens Design", Lens Talk, vol. 27, No. 3, Jan. 1998, pp. 1-4.

OPHTHALMIC LENS FOR CORRECTING ASTIGMATISM

FIELD AND BACKGROUND OF THE INVENTION

This application is a national phase of PCT/NL2014/050691, filed Oct. 6, 2014, and claims priority to EP 13187458.8, filed Oct. 4, 2013, the entire contents of both of which are hereby incorporated by reference.

The invention relates to ophthalmic lenses for correcting astigmatism to be worn in or on the eye.

A typical healthy human eye has a spherical curvature over all meridians (lines of intersection with planes in which the optical axis extends) of the cornea. A common defect in the human eye is astigmatism, which is usually caused by a difference in curvature of the cornea over meridians in planes oriented at different angles. Usually the largest difference is found between meridians at an angle of 90° relative to each other. In young eyes typically most curvature is found in the vertical meridian, in older eyes typically most curvature is found in the horizontal meridian—in both cases orientations refer to eyes in the head in a normal upright position, e.g. of a standing or seated person.

Approximately 22% of cataract patients have a corneal astigmatism of 1.5 D or more. Approximately 2% have a corneal astigmatism of 4.0 D or more (Zaldanha et al. Postoperative rotation of a 3-piece loop-haptic acrylic intraocular lens. J Cataract and Refr Surg 2009;35:1751-5). Such astigmatism can be corrected by refraction inverse to the astigmatism through intraocular lenses having a toric shape. In phakic eyes (in which the natural lens is present), astigmatism can also be corrected by intraocular lenses, such as applicant's Artiflex Toric lenses, toric contact lenses or spectacle lenses.

From European patent application 0 742 461, a toric lens is known in which a toric front (anterior) or back (posterior) surface of the lens is constructed with aspheric radii in which an equation including apical vertex curvature (inverse of radius at apex) and conic constant (asphericity) parameters describes each of the prime meridians. Thus, a toric surface is obtained of which the main meridians have different prescriptions and are aspheric for providing a depth-of-focus that allows cylindrical misalignment of up to 20 degrees from the reference 90 degree or 180 degree positions so that a smaller number of lens variants for different cylinder orientations is sufficient for accommodating to variations in cylinder orientation of a patient population. However, a trade-off of depth-of-focus is reduced contrast.

Also in US 2006/0116763, aspheric intraocular lenses are described, which are shaped such that, when implanted in an eye, lens and cornea, in combination, exhibit a peak calculated modulation transfer function (MTF) contrast of at least about 0.25 and a depth of field of at least about 0.75 diopters for pupil diameters in a range of about 4.5 mm to about 5 mm for monochromatic light at a wavelength of about 550 nm. In one embodiment, the intraocular lens has one or two toric refractive surfaces that exhibit two different optical powers along two orthogonal surface directions, each with a selected degree of asphericity such that a combination of the lens and the eye in which the lens is implanted provides not only a useful image contrast, but also a depth of field as described for other (non-toric) embodiments. The depth of field of an eye in which such a lens is implanted is much higher than the depth of field of the natural eye as for instance reported in "The depth-of-field of the human eye from objective and subjective measurements"; Susana Marcos, Esther Moreno, Rafael Navarro; Vision Research 39 (1999) 2039-2049.

From European patent application 1 903 986, an intraocular lens with a toric surface on its front surface as well as on its back surface is known. Also in this lens, the shape of the main meridians is described by an equation including the radii at apex and asphericity parameters. The radius at apex and asperities of intermediate meridians between the main meridians is determined as a sinusoidal function of the respective values of the main meridians, dependent on the angle of the intermediate meridian relative to the main meridians. Manufacturing a lens with toric surfaces on both sides increases manufacturing complexity and costs.

Current toric intraocular lenses and contact lenses comprising aspheric toric surfaces introduce additional aberrations into the human pseudo phakic optical system. In particular, such aberrations increase with the pupillary opening when a larger lens surface is involved in refracting light onto the retina. Since the pupillary opening is generally larger in low light circumstances, this entails that contrast deteriorates the more it is needed for adequate vision in view of unfavourable lighting conditions, so that night time visual acuity and light perception is adversely affected.

SUMMARY OF THE INVENTION

It is an object of the present invention to provide a lens for correcting astigmatism to be worn in or on the eye that introduces less aberrations than currently known lenses and in particular in which aberrations are more constant when the size of pupillary opening varies.

According to the invention, this object is achieved by providing a lens according to claim 1.

Because the main meridians and at least one meridian between the main meridians each have a different Coddington shape factor and a different asphericity that is related to the Coddington shape factor of the respective meridian in accordance with a relationship providing aberration neutral refraction for the respective meridian, an aberration neutral lens is obtained of which the effective dioptric power is very constant along each meridian from the optic axis to the periphery of the lens and the amount of aberrations varies very little with the pupillary opening determining over which surface portion of the lens light is refracted to the retina.

Particular elaborations and embodiments of the invention are set forth in the dependent claims Further features, effects and details of the invention appear from the detailed description and the drawings.

DETAILED DESCRIPTION

Figure 1:
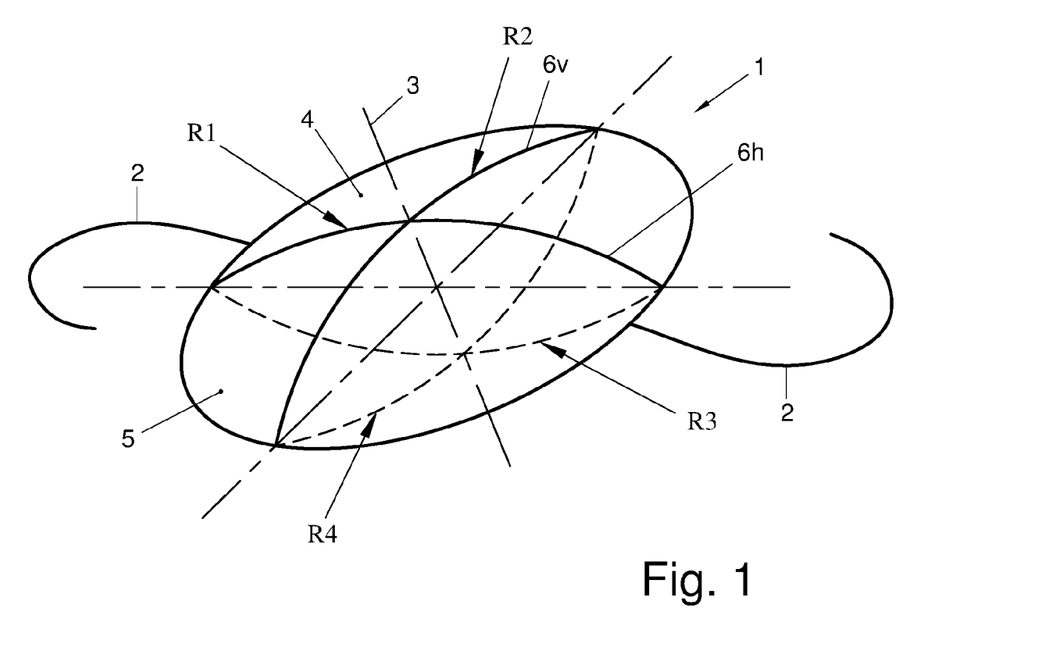
FIG. 1 is a schematic perspective view of a first example of a lens according to the invention.
Figure 2:
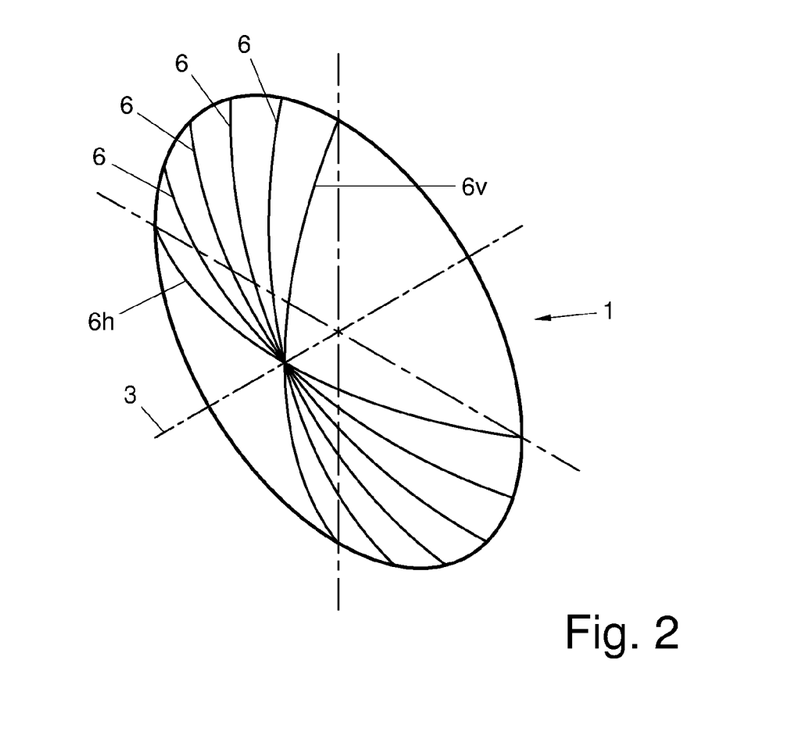
FIG. 2 is a schematic perspective view of a front surface of the lens according to FIG. 1.

In FIGS. 1 and 2 an example of a lens 1 according to the invention is schematically shown. The lens may be a contact lens with provisions for maintaining its orientation about the optical axis 3 or may be provided with haptics 2 for placement in an anterior or posterior chamber of a human eye. The front and rear lens surfaces 4, 5 intersect planes in which the optical axis 3 extends along meridians 6.

The meridians are curved such that each meridian has a constant dioptric power over its entire length within the optical portion of the lens. The lens may also have a peripheral non optical portion, for instance to smooth out the lens thickness to an edge shape with desired characteristics, for instance relating to placement in or on the eye.

In FIGS. 1 and 2 the main meridians extend vertically and horizontally and are designated by reference numerals 6v and 6h respectively. In the present example, the planes of the main meridians are perpendicular to each other, but the planes of the main meridians 6v, 6h may also intersect at other angles. The apex radii of the main meridians 6v, 6h are different from each other and the apex radii of the meridians 6 inbetween are between the apex radii of the main meridians 6v, 6h. Accordingly, the lens has a first dioptric power over the first main meridian 6v and a second dioptric power different from the first dioptric power over the second main meridian 6h. Over each meridian between the first and second main meridians, the lens has a dioptric power between the first dioptric power and the second dioptric power, the optical power continuously varying in circumferential sense from meridian to meridian.

The main meridians 6v, 6h and at least one meridian 6 between the main meridians 6v, 6r each have a different Coddington shape factor and a different degree of asphericity that is related to the Coddington shape factor of the respective meridian in accordance with a relationship providing aberration neutral refraction for the respective meridian 6v, 6h, 6.

This results in a very constant effective optical power over each entire meridian and accordingly a circumferentially averaged optical power that is constant from the optical axis to the periphery of the optical area of the lens. Preferably, the angle between the meridians between the main meridians that are shaped to an aberration neutral asphericity matching the individual Coddington shape factor of that meridian is infinitely small, so that also the asphericity continuously matches the Coddington shape factor for aberration neutral refraction over the entire meridian.

The appearance of the surface is not a constant radius but a curvature like shape, as the shape of the meridians continuously changes in circumferential sense from meridian to meridian. The optical performance is the integrated function of the meridians and thereby becomes constant over the meridians.

The slope in circumferential sense is gradual and falls less rapidly from the highest levels than with a lens design based upon smoothing between the flattest and most curved main meridians.

With the proposed lens, a visual acuity with very constant focal depth is achieved by not introducing additional spherical aberrations (and accordingly not adding focal depth/depth of field) to the pseudo phakic system, and with pupillary aperture independent optical performance, in particular a high contrast and resolution at large apertures that are typically associated to low lighting when these properties are most important for adequate vision.

As will be illustrated by the example discussed below, the invention can also be embodied in a multifocal lens having zones with different focal distances of which one or more zones are shaped for correction of astigmatism and with meridians of which the asphericity is matched to the Coddington shape factor of that meridian for aberration neutral refraction over the entire meridian. The invention can also be embodied in an accommodating lens.

The shape of the front meridians $R_1$, $R_2$ and back curvatures $R_3$, $R_4$ targeting the relevant toric power resulting in an aberration free constant meridian power, preferably for each meridian. The total optical power integrated in circumferential sense is constant from the optical axis to the outer edge of the optical portion of the lens.

The curvature of the continuous the optic can be calculated using the following equations;

Sagittal (anterior or posterior) surface dimensions are described using the following equation:

$$y_\alpha = \pm (x^2/r_1)/(1+(1-(K\alpha+1)*x^2/r_1^2)^{0.5}) \quad (1)$$

Where:

$y_\alpha$=sagittal height of point on meridian (varies by angle of meridian).

x=distance to optical axis on each meridian $r_1$=radius at apex of each meridian (varies by dioptric power)

$K_\alpha$=conic constant of each meridian (varies by angle of meridian).

Note1: $y_\alpha$ can be calculated by any equation that accomplishes the aberration neutral effect.

Note2: the increments of angle (α) for which the surface dimensions are calculated are chosen as small as required to accomplish the desired level of the continuous aberration neutral effect.

The conicity value $K_\alpha$(asphericity) of each meridian is related to the optical shape:

The Coddington shape factor for each meridian is:

$$Q_\alpha = (r_2+r_1)/(r_2-r_1) \quad (2)$$

Note3: $Q_\alpha$ can be calculated by any equation that describes shape variability.

Figure 3:
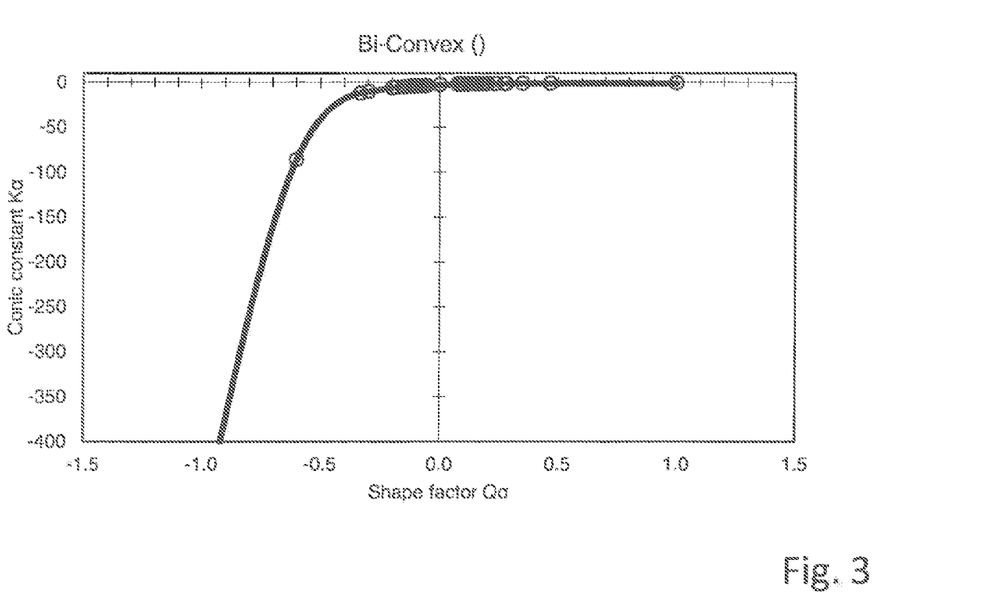
FIG. 3 is a graph of a relationship between the Coddington shape factor and conic constant of asphericity for an aberration neutral meridian of a biconvex lens.
Figure 4:
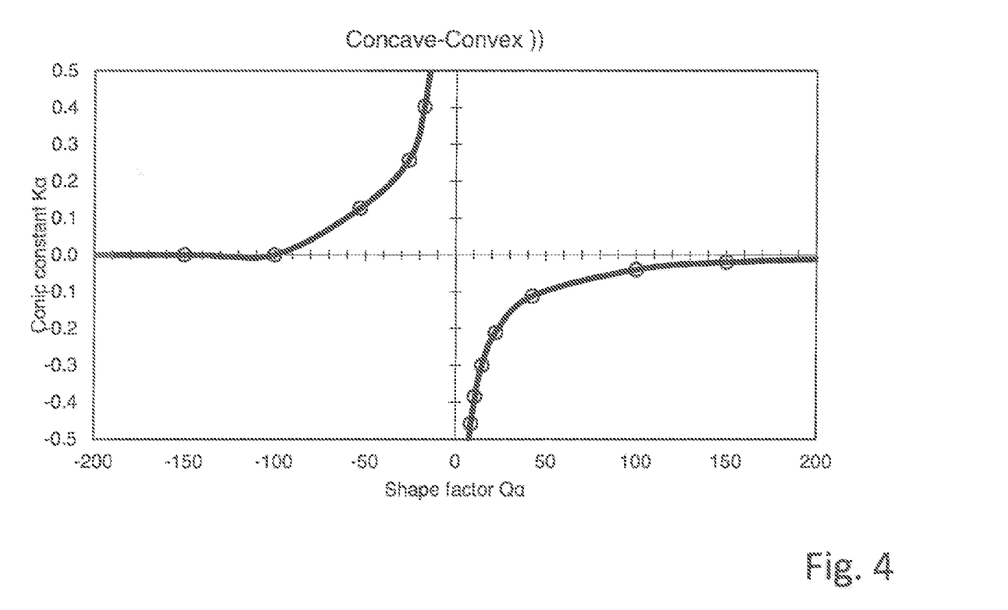
FIG. 4 is a graph of a relationship between the Coddington shape factor and conic constant of asphericity for an aberration neutral meridian of a concave-convex lens.

Where:

$Q_\alpha$=Coddington shape factor at each angle of meridian $r_1$=radius of 1st (anterior) side at each meridian $r_2$=radius of 2nd (posterior) side at each meridian To derive graphs for $K_\alpha$ as shown in FIGS. 3 and 4 a best fit to plotted graphs is calculated for each angle.

An example of how a lens shape according to the invention may be derived is discussed with reference to the graphs shown in FIGS. 5-11.

Figure 5:
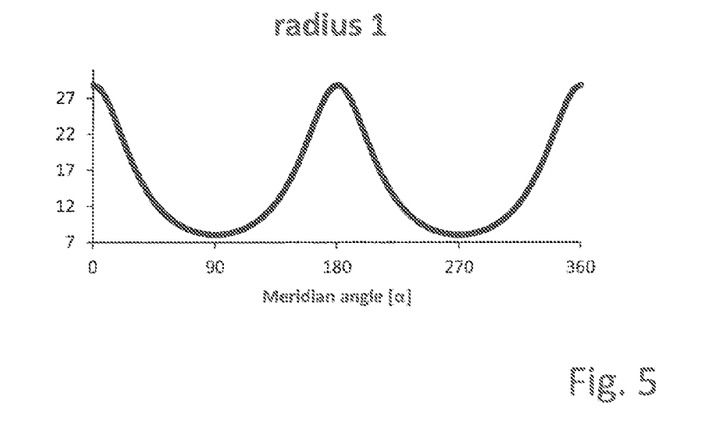
FIG. 5 is a graph of apex radii vs. angle α of a first surface of an example of a lens according to the invention.
Figure 6:
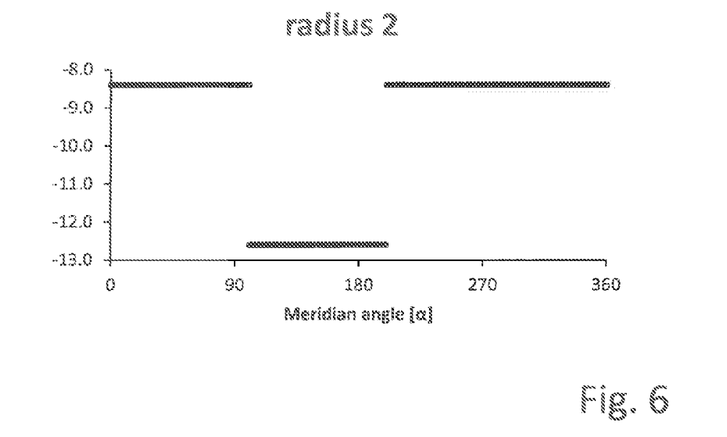
FIG. 6 is a graph of apex radii vs. angle α of a second surface opposite the first surface of an example of a lens according to the invention.

The apex radii in FIGS. 5 and 6 are for meridians with an angle α relative to a main (e.g. vertical) main meridian and provide a toric lens of which the front surface (radius 1) provides a 10 D cylinder correction. The rear surface is spherical (non-toric) and has a section with a power deviation of −5 D between 100 and 200 degrees to show the effect of the calculations and to illustrate application to a multifocal lens.

Figure 7:
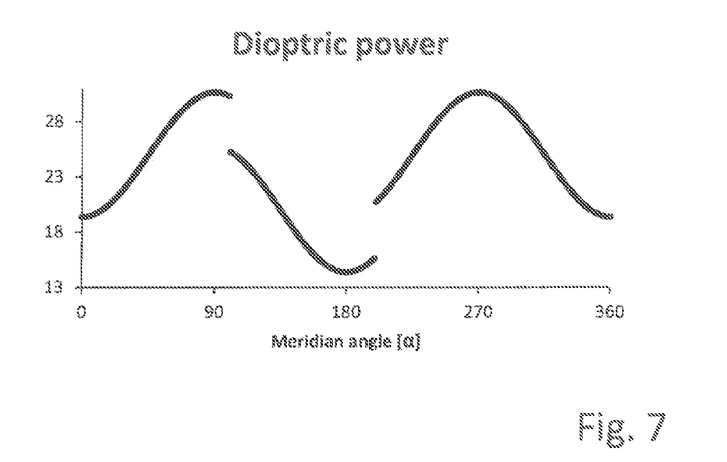
FIG. 7 is graph of basic dioptric power vs. angle α of a lens resulting from the apex radii according to FIGS. 5 and 6.
Figure 8:
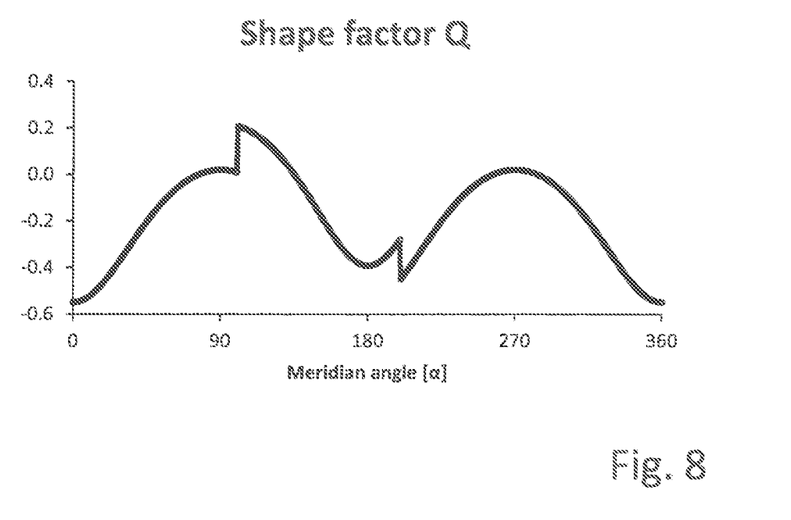
FIG. 8 is graph of basic Coddington shape factor Q vs. angle α of a lens resulting from the apex radii according to FIGS. 5 and 6.
Figure 9:
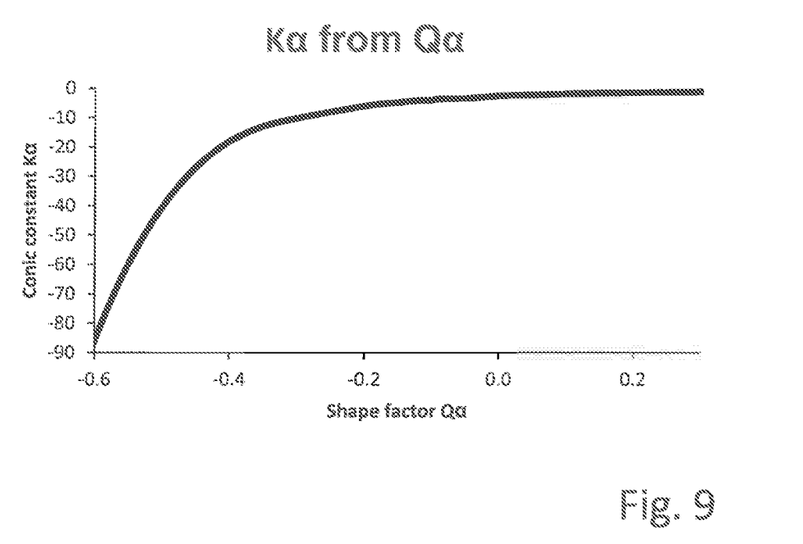
FIG. 9 is an enlarged view of a portion of the graph shown in FIG. 1 plotting Conic K factor of asphericity values for obtaining an aberration neutral meridian against Coddington shape factor values.
Figure 10:
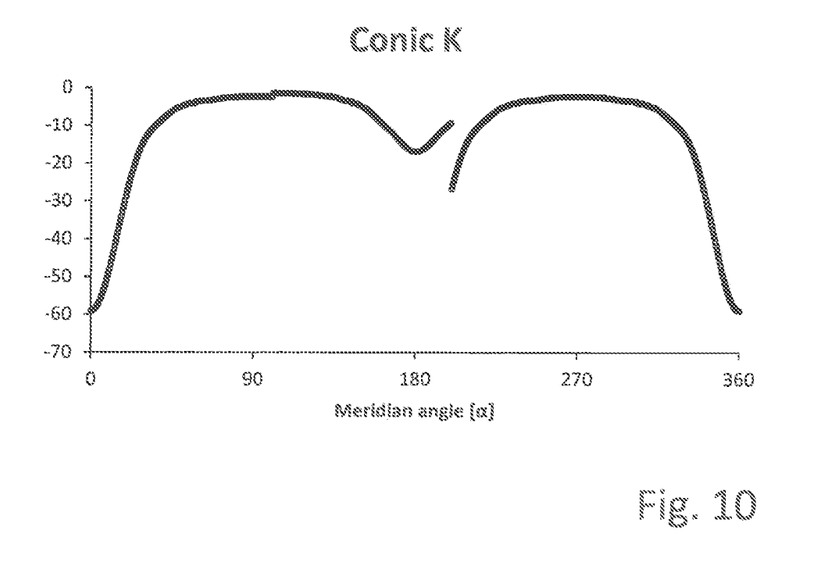
FIG. 10 is graph of Conic K factor of asphericity vs. angle α of a lens resulting from the Coddington shape factor Q vs. angle α according to FIG. 8 and the Conic K factor of asphericity values for obtaining an aberration neutral meridian against Coddington shape factor values of FIG. 9.
Figure 11:
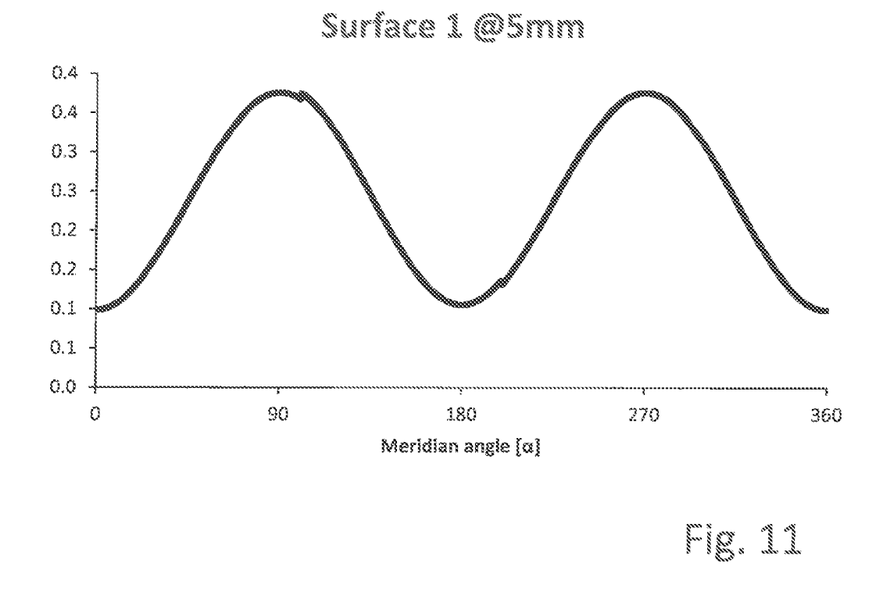
FIG. 11 is a graph of sag at 5 mm vs. angle of the first surface of a lens surface shape according to FIGS. 5-10.

The front and rear radii at apex according to the graphs shown in FIGS. 5 and 6 result in a basic dioptric power graph over angles α as shown in FIG. 7 and a Coddington shape factor Q over the angles α as shown in FIG. 8. To achieve aberration neutral refraction over each meridian the conicity factor $K_\alpha$ should be related to the Coddington shape factor Q in accordance with the graph shown in FIG. 9. Applied to the Coddington shape factor graph of FIG. 8, this results in a graph of conicity factor $K_\alpha$ over angles α as shown in FIG. 10. Thus, the radius and conicity (asphericity) parameters for calculating the aberration neutral shape of each front surface (surface 1) meridian oriented at any angle α are available. When applied, a surface 1 is obtained of which the sag at 5 mm from the optical axis varies in circumferential sense over the angle α as is shown in FIG. 11.

This continuous aberration neutral method described above is applicable to full meridians, semi-meridians or parts of meridians.

As can be seen from FIG. 7, the dioptric power graph over angles α is sinus shaped, apart from steps in optical power at borders between zones for near and far vision of the multifocal lens according to the present example. The amplitude of the sinusoidal pattern of optical power as a function of meridian angle α is the same, regardless of the distance to the optical axis of the lens along which the optical power is measured. In a lens according to the invention, also the transitional conic profile of the sag at 5 mm from the optical axis of the first surface as a function of meridian angle α approximates a perfect sinus shape as is shown in FIG. 11. This results in areas with largest and smallest toric power extending over larger surface areas and wider widths than in current toric intraocular lenses, of which the amplitude of the sinusoidal pattern of optical power as a function of meridian angle α is different at different distances from the optical axis. Therefore a lens according to the invention is more forgiving to slight off axis positioning and to rotational misalignment of the correction axes of the toric lens relative to the axes of astigmatism of the eye. The transitional conic profile also avoids visual disturbances due to aberrations once off axis.

A further advantage of a lens according to the invention is that an aberration neutral refraction can be achieved by toric aspheric shaping on one side and while the other side may be flat or of a conventional spherical shape, because aberration neutral asphericity can be made to follow variations in the shape factor caused by differences in the shapes of the front and rear surfaces. Lenses with a flat or spherical surface on one side can be manufactured more easily than lenses having a toric or toric and aspheric surface on both sides.

Furthermore, the invention allows shaping a multifocal lens in a relatively simple manner by forming aspheric zones with different radii in a first surface and providing an aberration neutral asphericity in the opposite surface, which is matched to the changes in the Coddington shape factor at the transition between the zones with different radii in the first surface. Thus additional aberrations due to zones with different focal distances can be reduced or avoided.

COMPARATIVE EXAMPLE

To intraoperatively compare the effect of misalignment of a lens according to the invention and a conventional toric lens, a lens according to the invention, was compared with a conventional lens (a "Lentis Toric" lens, commercially available from Oculentis GmbH, Berlin, Germany) on refraction by means of intraoperative wavefront aberrometry.

In a prospective, randomized, comparative study, patients with cataract and pre-existing corneal astigmatism underwent routine cataract surgery with bilateral implantation of a toric intraocular lens.

Intraoperative wavefront aberrometry, performed with an Optiwave

Refractive Analysis (ORA) system, was used to assess the effect of lens misalignment on cylinder reduction after which the lenses were rotated to the intended axis and surgery was completed.

Emmetropia was targeted. Intraoperative refraction was measured at 10°, 5° and at 0° misalignment using the ORA system wavefront aberrometer (WaveTec Vision Systems, Aliso Viejo, Calif., USA). Uncorrected (UDVA) and corrected (CDVA) distance visual acuities, refraction and lens misalignment were evaluated one month postoperatively. Postoperative lens misalignment was assessed using a KR-1W Wavefront analyzer (Topcon, Tokyo, Japan).

Toric intraocular lens implantation in 10 eyes in each subgroup resulted in an average of 1.6° rotational misalignment with the lens according to the invention and an average rotational misalignment of 2.2° with the Lentis Toric lens.

Conventionally, every degree of rotational misalignment of an intraocular lens results in a decrease of the correction of astigmatism of about 3.3%. If a toric intraocular lens is misaligned by 10°, the astigmatism will remain 33% undercorrected. If a toric intraocular lens is misaligned by 30°, typically no correction of astigmatism is achieved.

This known relationship between undercorrection and misalignment was also found in the Lentis Toric lens at rotational misalignments of 10° (33% undercorrection) and 5° (16% undercorrection).

Rotational misalignment of the lens according to the invention of 10° resulted in an average undercorrection of astigmatism of 18% instead of 33%, as would be expected from a conventional toric intraocular lens, and the average undercorrection at 5° rotational misalignment was 9%, instead of 17% as would be expected from a conventional toric intraocular lens.

The invention claimed is:

1. An ophthalmic lens to be worn on or in a human eye for refractive correction of astigmatism, the lens having an anterior surface and a posterior surface, the anterior surface and the posterior surfaces being shaped such that at least a zone of said lens said lens has:
   a first dioptric power over a first main meridian:
   a second dioptric power different from said first dioptric power over a second main meridian intersecting said first meridian; and
   a dioptric power between said first dioptric power and said second dioptric power over each meridian between said first and second main meridians, said optical power continuously varying from meridian to meridian;

wherein the main meridians and at least one meridian between the main meridians each have a different Coddington shape factor and a different asphericity that is related to the Coddington shape factor of the respective meridian in accordance with a relationship providing aberration neutral refraction for the respective meridian.

2. A lens according to claim 1, wherein a plurality of meridians between the main meridians each have a different Coddington shape factor and a different asphericity that is related to the Coddington shape factor of the respective meridian in accordance with a relationship providing aberration neutral refraction for the respective meridian.

3. A lens according to claim 2, wherein each meridian between two subsequent ones of the main meridians has a different Coddington shape factor and a different asphericity that is related to the Coddington shape factor of the respective meridian in accordance with a relationship providing aberration neutral refraction for the respective meridian.

4. A lens according to claim 1, wherein the anterior surface or the posterior surface is flat or of spherical shape.

5. A lens according to claim 1, wherein the anterior surface or the posterior surface has a first zone that is flat or of a spherical shape and a second zone that is flat or of a spherical shape, the first zone having a different radius of curvature than the second zone.

6. A lens according to claim 5, wherein dioptric power varies over angles α between the first dioptric power over the first main meridian and the second dioptric power over the second main meridian as at least one sinusoidal function in each of said first and second zones, the amplitude of said function being the same for optical powers measured at different distances from the optical axis.

7. A lens according to claim 1, wherein dioptric power varies over angles α between the first dioptric power over the first main meridian and the second dioptric power over the second main meridian as at least one sinusoidal function, the amplitude of said function being the same for optical powers measured at different distances from the optical axis.

8. An ophthalmic lens to be worn on or in a human eye for refractive correction of astigmatism, the lens having an anterior surface and a posterior surface, the anterior surface and the posterior surfaces being shaped such that at least a zone of said lens said has:
   a first dioptric power over a first main meridian:
   a second dioptric power different from said first dioptric power over a second main meridian intersecting said first meridian; and
   a dioptric power between said first dioptric power and said second dioptric power over each meridian between said first and second main meridians, said optical power continuously varying from meridian to meridian;
   wherein the main meridians and at least one meridian between the main meridians each have a different Coddington shape factor and a different asphericity that is related to the Coddington shape factor of the respective meridian in accordance with a relationship providing aberration neutral refraction for the respective meridian,
   wherein the anterior surface or the posterior surface is flat or of spherical shape, and wherein the surface opposite of the flat or spherical anterior or posterior surface has a conic profile of which sag at 5 mm from the optical axis is a sinusoidal function of meridian angle α.

\* \* \* \* \*